(12) United States Patent
Gil Ramos et al.

(10) Patent No.: US 11,869,662 B2
(45) Date of Patent: Jan. 9, 2024

(54) UPDATING LEARNED MODELS (71) Applicant: Nokia Technologies Oy, Espoo (FI)

(72) Inventors: Alberto Gil Ramos, Cambridge (GB); Sourav Bhattacharya, Cambridge (GB); Nicholas Lane, Cambridge (GB); Fahim Kawsar, Cambridge (GB)

(73) Assignee: NOKIA TECHNOLOGIES OY, Espoo (FI)

( * ) Notice: Subject to any disclaimer, the term of this patent is extended or adjusted under 35 U.S.C. 154(b) by 467 days.

(21) Appl. No.: 16/954,921

(22) PCT Filed: Dec. 10, 2018

(86) PCT No.: PCT/EP2018/084092
§ 371 (c)(1),
(2) Date: Jun. 17, 2020

(87) PCT Pub. No.: WO2019/121083
PCT Pub. Date: Jun. 27, 2019

(65) Prior Publication Data
US 2020/0394465 A1    Dec. 17, 2020

(30) Foreign Application Priority Data
Dec. 20, 2017  (EP) .................................... 17208716

(51) Int. Cl.
*G16H 50/20*     (2018.01)
*G16H 40/67*     (2018.01)
(Continued)

(52) U.S. Cl.
CPC ......... *G16H 50/20* (2018.01); *G06F 18/2148* (2023.01); *G06F 18/2155* (2023.01);
(Continued)

(58) Field of Classification Search
CPC ...... G06K 9/6259; G16H 40/67; G16H 10/60; G16H 50/70; G06N 20/00
See application file for complete search history.

(56) References Cited

U.S. PATENT DOCUMENTS 6,238,337 B1    5/2001   Kambhatla et al.
8,062,220 B2   11/2011   Kurtz et al.
(Continued)

FOREIGN PATENT DOCUMENTS

EP         3483792 A1    5/2019
WO    2018/017467 A1    1/2018

OTHER PUBLICATIONS

Office action received for corresponding European Patent Application No. 17208716.5, dated Jan. 3, 2022, 11 pages.
(Continued)

*Primary Examiner* — David E Choi
(74) *Attorney, Agent, or Firm* — ALSTON & BIRD LLP (57) ABSTRACT

Methods and systems are disclosed for updating learned models. An embodiment comprises receiving a plurality of data sets representing sensed data from one or more devices and determining, using one or more local learned models, local parameters based on the received data sets. Another operation may comprise generating a combined data set by combining the plurality of data sets and, determining, using one or more local learned models, global parameters based on the combined data set. Another operation may comprise transmitting, to a remote system, the global parameters for determining updated global parameters using one or more global learned models based at least partially on the global parameters, and receiving, from the remote system, the updated global parameters. Another operation may comprise updating the one or more local learned models using both the local parameters and updated global parameters.

18 Claims, 5 Drawing Sheets (51) Int. Cl.
  *G16H 10/60* (2018.01)
  *G16H 50/70* (2018.01)
  *G06N 20/00* (2019.01)
  *G06F 18/214* (2023.01)

(52) U.S. Cl.
  CPC ............ *G06N 20/00* (2019.01); *G16H 10/60* (2018.01); *G16H 40/67* (2018.01); *G16H 50/70* (2018.01)

(56) References Cited

U.S. PATENT DOCUMENTS

| | | | |
|---|---|---|---|
| 9,665,654 | B2 | 5/2017 | Duncker et al. |
| 2003/0135391 | A1 | 7/2003 | Edmundson et al. |
| 2010/0169108 | A1 | 7/2010 | Karkanias et al. |
| 2013/0226838 | A1 | 8/2013 | Chu et al. |
| 2013/0238348 | A1 | 9/2013 | Kim |
| 2013/0262059 | A1 | 10/2013 | Grbovic et al. |
| 2015/0242760 | A1* | 8/2015 | Miao ................ G06N 20/00 706/12 |
| 2015/0324690 | A1 | 11/2015 | Chilimbi et al. |
| 2016/0063393 | A1* | 3/2016 | Ramage ............ H04L 67/1396 706/12 |
| 2017/0109322 | A1* | 4/2017 | McMahan ............ G06N 20/00 |
| 2017/0169358 | A1* | 6/2017 | Choi ................ G06N 20/00 |
| 2018/0234302 | A1* | 8/2018 | James ............... G06N 20/00 |
| 2019/0372859 | A1* | 12/2019 | Mermoud ........... G06F 21/6245 |
| 2020/0394465 | A1* | 12/2020 | Gil Ramos ............ G16H 50/70 |
| 2021/0345134 | A1* | 11/2021 | Ottersten ............. H04W 16/22 |
| 2023/0027149 | A1* | 1/2023 | Kuan .................. H04L 63/1425 |

OTHER PUBLICATIONS

McMahan et al."Communication-Efficient Learning of Deep Networks from Decentralized Data", arXiv, Feb. 28, 2017, 11 pages.

Mizukura et al., "New Application of IEEE 11073 to Home Health Care", The Open Medical Informatics Journal, vol. 3, 2009, pp. 44-53.

Extended European Search Report received for corresponding European Patent Application No. 17208716.5, dated Jun. 15, 2018, 15 pages.

International Search Report and Written Opinion received for corresponding Patent Cooperation Treaty Application No. PCT/EP2018/084092, dated Mar. 8, 2019, 20 pages.

Office Action for Chinese Application No. 201880087354.0 dated Mar. 17, 2023, 16 pages.

* cited by examiner

UPDATING LEARNED MODELS

RELATED APPLICATION

This application claims priority to PCT Application No. PCT/EP2018/084092, filed on Dec. 10, 2018, which claims priority to European Application No. 17208716.5, filed on Dec. 20, 2017, each of which is incorporated herein by reference in its entirety.

FIELD

The present specification relates to updating learned models, for example for use in data analytics based on sensed data such as that produced by portable data sensing devices.

BACKGROUND

Systems for training machine learning models to provide analytics are known. Such systems generally fall into two broad categories.

The first category is a centralized training model whereby raw user data is updated to an external server. The raw data is used to train the model and provide analytics. The second category is a decentralised training model whereby raw user data is converted into parameter updates for training the model on a user device. The parameter updates are then sent to an external server to train the model and provide analytics.

SUMMARY

In a first aspect, the specification describes an apparatus comprising: means for receiving a plurality of data sets representing sensed data from one or more devices; means for determining, using one or more local learned models, local parameters based on the received data sets; means for generating a combined data set by combining the plurality of data sets; means for determining, using one or more local learned models, global parameters based on the combined data set; means for transmitting, to a remote system, the global parameters for determining updated global parameters using one or more global learned models based at least partially on the global parameters; means for receiving, from the remote system, the updated global parameters; and means for updating the one or more local learned models using both the local parameters and updated global parameters.

In the first aspect, the apparatus may further comprise: means for transmitting, to the one or more devices, the updated one or more local learned models.

In the first aspect, the one or more devices are members of a predetermined group of devices.

In the first aspect, the apparatus may further comprise: means for identifying from which device each of the plurality of data sets is received from such that the generated local parameters are particular to each of the identified devices.

In the first aspect, at least one of the received data sets comprises at least one missing data field, and the apparatus may further comprise: means for inferring and inserting the at least one missing data field using the one or more local learned models.

In the first aspect, the apparatus may further comprise: means for normalizing the plurality of data sets; and means for using the plurality of data sets to capture high-order correlations.

In the first aspect, the apparatus may further comprise: means for combining the local parameters and the updated global parameters; and means for updating the one or more local learned models using the combined parameters.

In the first aspect, the apparatus may further comprise: means for combining the plurality of data sets with one or more historical data sets.

In the first aspect, the plurality of data sets corresponds to different users of a single device.

In the first aspect, the plurality of data sets correspond to a single user of different respective devices.

In the first aspect, the data sets represent sensed health or activity data.

In the first aspect, the one or more devices are portable health monitoring devices and wherein the data sets are received wirelessly from one or more health monitoring devices.

In the first aspect, the apparatus is a hub device and wherein the data sets are received from the one or more devices in local network.

In a second aspect, the specification describes a method comprising: receiving a plurality of data sets representing sensed data from one or more devices; determining, using one or more local learned models, local parameters based on the received data sets; generating a combined data set by combining the plurality of data sets; determining, using one or more local learned models, global parameters based on the combined data set; transmitting, to a remote system, the global parameters for determining updated global parameters using one or more global learned models based at least partially on the global parameters; receiving, from the remote system, the updated global parameters; and updating the one or more local learned models using both the local parameters and updated global parameters.

In a third aspect, the specification describes a computer readable medium comprising computer program code stored thereon, the computer readable medium and computer program code being configured to, when run on at least one processor: receive a plurality of data sets representing sensed data from one or more devices; determine, using one or more local learned models, local parameters based on the received data sets; generate a combined data set by combining the plurality of data sets; determine, using one or more local learned models, global parameters based on the combined data set; transmit, to a remote system, the global parameters for determining updated global parameters using one or more global learned models based at least partially on the global parameters; receive, from the remote system, the updated global parameters; and update the one or more local learned models using both the local parameters and updated global parameters.

Preferred features of the first aspect may also be applied to the second and third aspects.

BRIEF DESCRIPTION OF THE DRAWINGS

Example embodiments will now be described, by way of non-limited examples, with reference to the following schematic drawings, in which.

DETAILED DESCRIPTION

Embodiments herein relate to updating learned models. Learned models are sometimes called learning models and form part of the general field of machine learning or artificial intelligence. Learned models may be based on dynamical systems and/or statistical models, for example, and generally operate according to one or more algorithms and model parameters.

A model parameter, hereafter "parameter", is a configuration variable that may be internal to the model and whose value can be estimated from data. Parameters may be required by the model to make predictions, and may be estimated or learned from the data as part of an optimisation algorithm to produce new or updated parameters. Parameters may be saved as part of the learned model and refined data may be generated as a result of updating the learned model. It will be appreciated however that parameters are different from the raw data that is applied or inputted to the learned model.

The models that are the subject of embodiments herein may be any form of learned model that predicts data based on inputted data. The models may be embodied in, for example, an artificial neural network.

Embodiments herein relate to updating such learned models in the context of user devices to and possibly wireless devices such as personal health monitoring devices. In this regard, it is becoming increasingly common for users to wear or otherwise carry portable wireless devices such as smart phones and smart watches. These devices have in-built sensors for measuring or monitoring health-related data such as walking steps, blood pressure and heart rate. Other devices which tend to be communal (and not worn) include weighing scales, which may measure an identified user's weight and/or body mass index (BMI). Communal devices are nevertheless typically portable. So-called smart beds for the tracking of, for example, sleep information are also considered a form of user device in this context.

Such devices tend to have in-built wireless transceivers for transmitting and receiving data using protocols such as WiFi, WiMAX and Bluetooth and any other communication method. The use of wireless communications is not considered essential, however.

For individual users, this sensed or measured 'raw' data may be applied to a learned model for various reasons. For example, there may be missing data in the received raw data sets. Such raw data sets may be referred to as sparse data sets. It is not uncommon for users to remove smart watches for a period of time and/or for smart phones to be left at home or in the office. Users may not weigh themselves regularly. Learned models may be used therefore to augment or fill-in gaps of missing data for users, transforming the sparse data into rich data using modelled data for the user and/or for the particular device. Also, the various remote devices may be heterogeneous and their data sets not necessarily compatible with one another. The learned models may therefore be used to integrate or normalise the data sets to assist in providing useful statistical analysis for users based on the collective data. For example, a learned model may provide a daily analysis of calories burned, based on data from a smart watch, smart phone and communal weighing scales, notwithstanding that this data may have missing data for a period of time and/or is received in different formats. Individual users may wish to see personalised analysis from such learned models.

The quality of the analysis produced by the learned models tends to improve by updating models with data from different data sources, possibly from other users. However, users may view their raw user data as sensitive and personal, and may not therefore wish to share this raw data with external updating systems where the data may be susceptible to interception over the transmission medium and/or at the external system. As the number of user devices grows, this also means that a potentially large amount of data will be sent to the external updating system over time. On the other hand, updating models at the user devices themselves using only the individual user's raw data will produce analysis data of limited quality and is further restricted by the limited processing power of such user devices.

In overview, embodiments herein provide for updating one or more learned models for a limited group of multiple users at one or more localised updating devices (these may, for example, be described as hubs). The one or more localised updating devices receive raw data from a limited set of user devices, e.g. belonging to a common household or group, which raw data may be encoded or encrypted to provide a level of security for the raw data as it passes from the portable devices to the localised updating device. The raw data may be processed at the localised updating device to generate local parameters used to update models for analytics based on applying the received raw data from the limited set of user devices to one or more locally stored models. The analytics provided to individual users may therefore take into account more than one set of raw data, which offers improvement. The analytics may be personalised to individual users, and may also provide aggregated analytics for the common household or group.

Furthermore, embodiments provide for generating another set of parameters, referred to herein as global parameters, for the combined group of users or devices for sending to an external remote server (hereafter "server") for producing updated global parameters. The server may also receive different sets of global parameters from other such groups, via their respective localised updating devices. This enables one or more sets of updated global parameters to be generated at the external remote server, potentially from a huge pool of users, based only on global parameters from the localised updating devices and not from raw data. The global update parameters can be sent back to the one or more localised updating devices for updating their local models using both the updated global and local parameters, which produces a higher quality of analysis over time and is readily scalable. This may be achieved without sending users' raw data to the external remote server, increasing confidence in the security of such raw data, and in a data efficient manner because the parameter updates will require less data than the raw data sets.

Conventionally, a problem with updating learned models is that sensed data is sent to an external server causing a lack of privacy because a user's raw data is sent over a potentially unsecure network. For example, a nefarious individual may be able to hack into the server and download and distribute the user's health data.

In order to combat the lack of privacy, the parameters, and not the raw data, might be sent to the server to update the one or more learned models. Therefore, the user's raw data is not sent to the server and a nefarious individual hacking into the server can only download parameters and not the user's raw data. However, because the external server only receives parameters, it is not able to provide users with individual and personal analytics and nor is it able to efficiently counteract a user's sparse raw data because it does not receive any raw data.

Embodiments herein provide for improved methods and systems.

Figure 1:
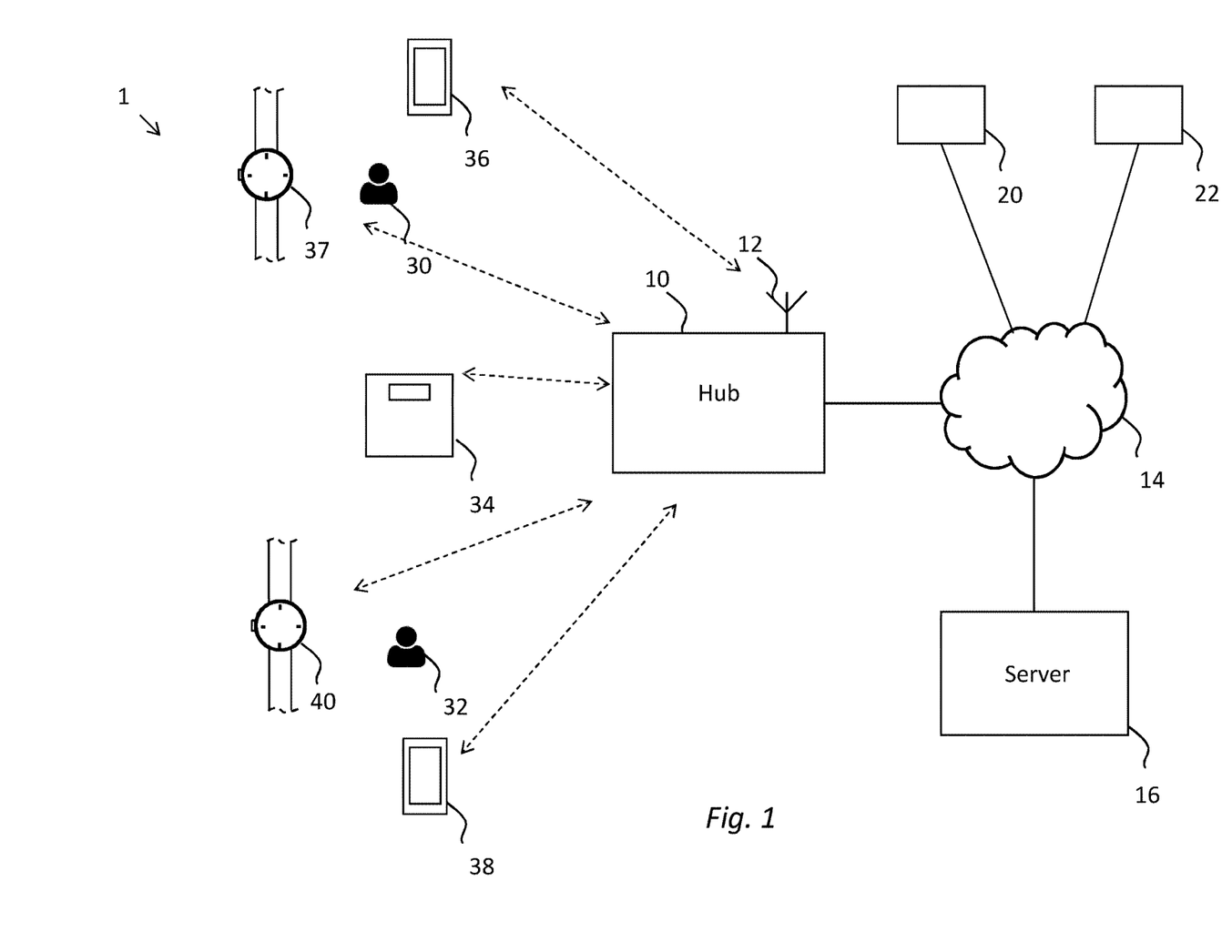
FIG. 1 is a diagram of a data communications network incorporating a system for updating learned models associated with user devices according to example embodiments.

FIG. 1 shows a system 1 according to one example embodiment, including a plurality of hubs 10, 20 and 22, user devices 34, 36, 37, 38, 40 and first and second users 30, 32. The system 1 also comprises a remote, external server 16, hereafter "server." The server 16 may be considered a cloud device.

A first hub 10 is configured to collect raw data from the one or more user devices 34, 36, 37, 38, 40. The first hub 10 may be connected to the server 16 via an IP network 14, which may be the Internet or any other type of network. The server 16 is configured to receive model parameters from the first hub 10, referred to herein as global parameters, and also global parameters from one or more other hubs 20, 22, which may be in respective different locations from the first hub and associated with other groups of users. The server 16 generates updated global parameters for updating local models of the first hub 10 and possibly the other hubs 20, 22, which hubs may subsequently update local models stored on the hubs.

User devices 37 and 40 are typically, but not necessarily, wearable devices such as smart watches or similar. User devices 37 and 40 may be used to capture health data or activity data such as the number of steps a user takes over a period of time. In another embodiment, the user devices 37 and 40 may alternatively or additionally be used to capture blood pressure and/or temperature of a user. User devices 37 and 40 are each typically used by a single user who may be associated with the respective user device via an application or configuration setting.

User devices 36 and 38 are shown as smart phones, respectively associated with the first and second users 30, 32.

User device 34 may be a communal device, used by the first and second users 30, 32 at different times, and may be a smart weight scale. User device 34 may be used to capture health data or activity data such as the weight of a user. In another embodiment, the user device 34 may be used to capture blood pressure and/or temperature of a user. The data generated by the user device 34 may identify the user currently using said device by means of biometrics or based on the current weight or other sensed parameter approximately correlating with one that is stored. This identifying may alternatively be performed at the first hub 10.

User devices 34, 36, 37, 38, 40 are typically a set of devices that have agreed to share their respective raw user data sets with the first hub 10. In an embodiment, the user devices 34, 36, 37, 38, 40 may belong to members of a common household, such as family members. Alternatively, the set of devices may belong to members of a common team. For instance, user devices 34, 36, 37, 38, 40 may register with the first hub 10 and provide a user name and password for registration with the first hub. This may be performed by a user using an application or a dedicated web page. The fact that certain users are members of a common team or group may be inferred, e.g. due to their proximity to the first hub 10, and/or through configuration via an application or a web page. For example, the first hub 10 may issue an identifying beacon, similar to a SSID, that a user may select on the respective device and be prompted to input an associated password that may be provided with the first hub or on associated literature. For example, one user may be set up as an administrator of the common team or group and permission may be required from said administrator in order to join the group. The administrator, or other users, may issue invitations to other users in some embodiments. In some embodiments, one or more of the first or second users 30, 32 may opt out of sending one or more selected data sets, such as weight, and allow the other data sets to be sent. This selection may be performed using an application or website configuration.

User devices 34, 36, 37, 38, 40 in use transmit users' raw data to the first hub 10. The raw data may be sent wirelessly over any communication network, and here the IP network 14 is used. In an embodiment, the raw data may be sent to the first hub 10 when the user devices 34, 36, 37, 38, 40 are in an idle mode or when the user devices are in a charging mode. This may not affect user experience and minimises when data is sent, for example to avoid discharging the battery which may be running low.

The first hub 10 may be a dedicated localised router. The first hub 10 may be configured periodically to receive raw user data from the user devices 34, 36, 37, 38, 40 and to identify from which user device 34, 36, 37, 38, 40 the raw data is received from. In some embodiments, the hub 10 may be configured to identify which of the first and second users 30, 32 a particular set of raw data belongs to.

The first hub 10 may comprise, for example on local memory, one or more local learned models that use the received raw data to generate local parameters that are used to update one or more local learned models. The one or more local learned models may also use the users' raw data to provide personalised analytics to each of the user devices 34, 36, 37, 38, 40 and/or to update one or more local models stored on said user devices so that said user devices can provide the personalised analytics. In an embodiment, the one or more local learned models are used to provide personalised analytics to each of the first and second users 30, 32 of the user devices 34, 36, 37, 38, 40.

The first hub 10 may also be configured to combine the raw data sets of the first and second users 30, 32 to generate a combined data set. The first hub 10 may also be configured to counteract sparse raw user data. For example, the hub may infer and insert any missing data into the combined data set to provide an enriched, or rich, data set.

In an embodiment, the first hub 10 may also store and incorporate historical data, i.e. data that has been received previously, into the combined data set. The first hub 10 may store raw data for a predetermined period of time so that it can use the historical raw data to generate a combined data set.

The first hub 10 may generate global parameters using the one or more local learned models. The global parameters may be generated by using the combined data set, which may be anonymised by removing identifiers for the first and second users 30, 32. The combined data set may only be identifiable as being associated with the first hub 10, or a user-defined label, such as "Family A." The first hub 10 may transmit the global parameters to the server 16. In this regard, no raw data is sent to the server, which may be vulnerable to attack. Nor is any means of identifying the first and second users 30, 32 provided. Therefore, the users' raw data is secured.

The server 16 may receive global parameters from the plurality of other hubs 20, 22. The server 16 includes one or more global learned models. The server 16 may update the one or more global learned models using the received global parameters from the hubs 10, 20, 22. Receiving a plurality of global parameters from the plurality of hubs 10, 20, 22 allows the one or more global learned models to be trained more effectively since more parameters, derived from a potentially large number of users, are available to the server 16.

The server 16 produces updated global parameters using the one or more global learned models. The server 16 transmits the updated global parameters to the first hub 10 and may also transmit these to the other hubs 20, 22.

As will be explained, as well as producing a set of global parameters, the first hub 10 may also use the one or more local learned models to produce updated local parameters particular to to each user device 34, 36, 37, 38, 40 and/or to each of the first and second users 30, 32. The first hub 10 may therefore combine the updated local parameters and the updated global parameters for updating the local learned models, and/or for updating models that may be stored on each user device 34, 36, 37, 38, 40 in order to produce data analytics based on both sets of updates. This enables the one or more local learned models to be updated based on a much larger pool of user data, making the models more accurate, but also in a personalised manner with respect to each user device 34, 36, 37, 38, 40 and/or with respect to each of the first and second users 30, 32 of the devices.

In an embodiment, the first hub 10 may transmit the one or more updated learned models to each of the appropriate user devices 34, 36, 37, 38, 40.

Figure 2:
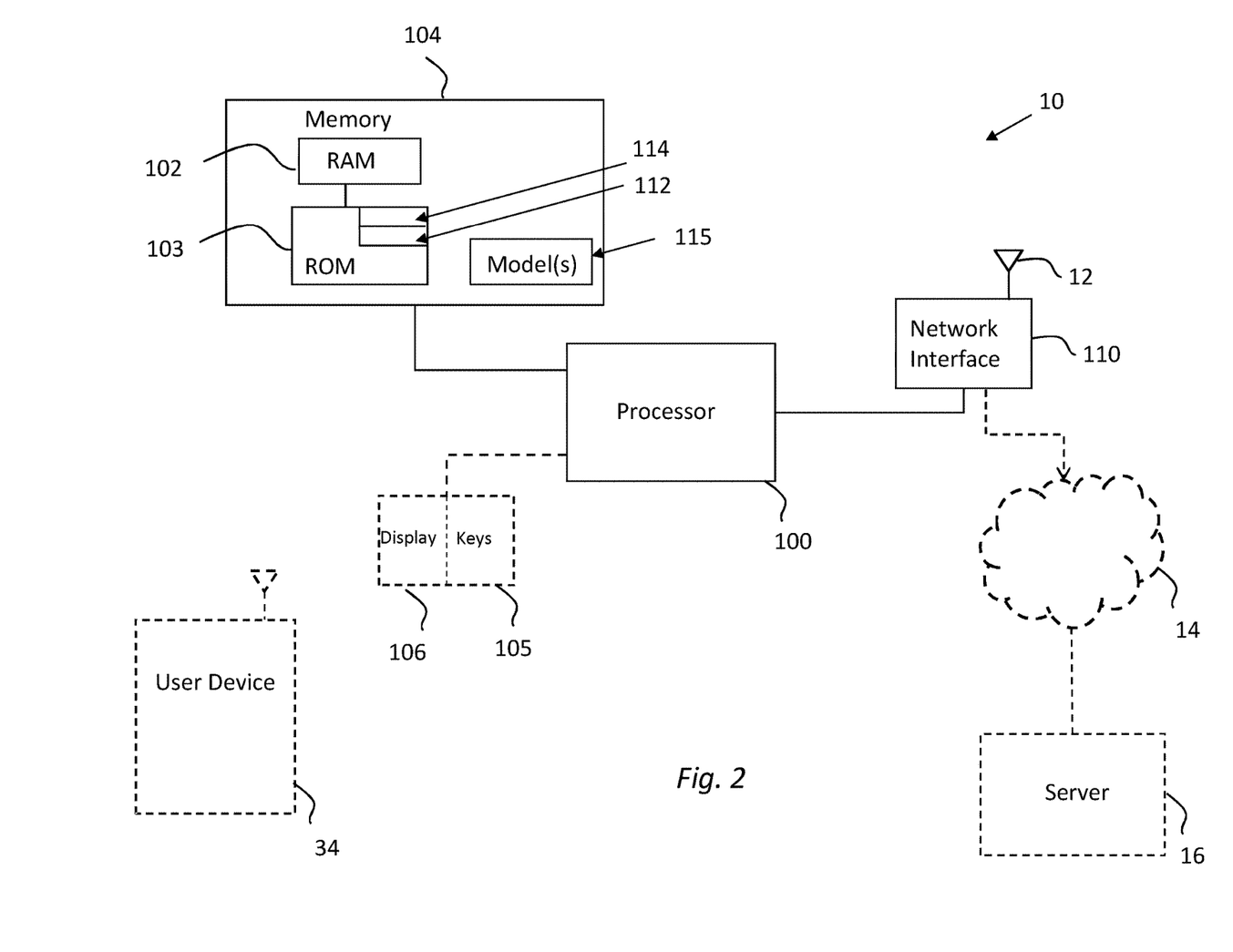
FIG. 2 is a schematic diagram of components of a hub forming part of the FIG. 1 system.

FIG. 2 is a schematic diagram of components of the first hub 10 shown in FIG. 1.

The first hub 10 may have a processor 100, a memory 104 coupled to the processor and comprised of a RAM 102 and ROM 103, and a network interface 110. It may comprise a display 106 and one or more hardware keys 105. The first hub 10 may comprise one or more network interfaces 110 for connection to a network, e.g. using Bluetooth or similar. The one or more network interfaces 110 may also be for connection to the internet, e.g. using WiFi or similar. The processor 100 is connected to each of the other components in order to control operation thereof.

The memory 104 may comprise a non-volatile memory, a hard disk drive (HDD) or a solid state drive (SSD). The ROM 103 of the memory 104 stores, amongst other things, an operating system 112 and may store software applications 114. The RAM 102 of the memory 104 may be used by the processor 100 for the temporary storage of data. The operating system 112 may contain code which, when executed by the processor, implements the operations as described below.

The memory 104 may also store one or more local learned models 115 which may be updated using methods described herein.

The processor 100 may take any suitable form. For instance, it may be a microcontroller, plural microcontrollers, a processor, or plural processors and it may comprise processor circuitry.

In some embodiments, the hub 10 may also be associated with external software applications. These may be applications stored on a remote device and may run partly or exclusively on the remote device. These applications may be termed, in some cases, cloud-hosted applications. The hub 10 may be in communication with the remote device in order to utilize the software application stored there.

A user device 34 shown in FIG. 1 is also shown for completeness, but does not form part of the first hub 10, and may be any one of the above-mentioned user devices 34, 36, 37, 38, 40. Similarly, the IP network 14 and server 16 is also shown for completeness but does not form part of the first hub 10.

Alternative to the FIG. 2 example, the methods and systems described herein may be implemented in hardware, software, firmware or any combination thereof.

Figure 3:
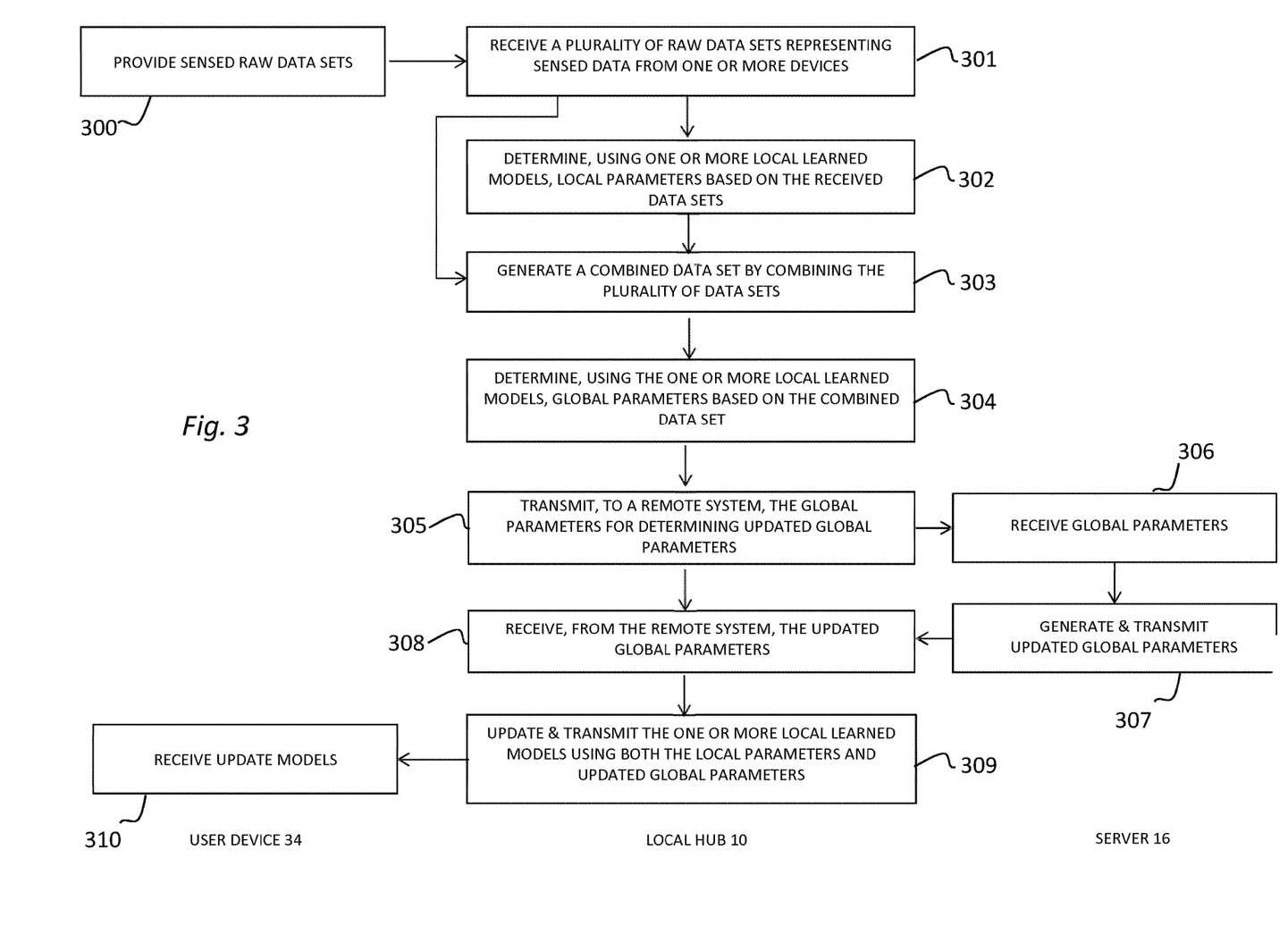
FIG. 3 is a flow diagram illustrating processing operations performed at an example user device, the hub shown in FIGS. 1 and 2, and a server, according to example embodiments.

FIG. 3 is a flow diagram illustrating respective example processing operations that may be performed by one of the user devices 34, the first hub 10 and the server 16. Certain operations may be omitted or replaced with others. Certain operations may be re-ordered.

A first operation 300, performed at the user device 34, comprises providing one or more sensed raw data sets, which may comprise one or more of heart rate, blood pressure and number of steps. The provided raw data sets are transmitted to the local hub 10 using any suitable method as mentioned above.

At the local hub 10, upon receipt of the raw data sets, an operation 301 comprises receiving the raw data sets. As will be appreciated, raw data sets may also be received from the other user devices 36, 37, 38, 40.

At this stage, which will be elaborated on below, further operations may comprise identifying from the received raw data sets which user devices 34, 36, 37, 38, 40 the raw data sets are derived from and/or which the first and second users 30, 32 the raw data sets come from. Further, if the raw data sets are sparse, or not in a standardised format, the one or more local learned models 115 may be applied to fill-in the missing data and/or to standardise the formats to generate respective rich data sets.

Another operation 302 may comprise generating, using the one or more local learned models 115, updated local parameters based on the received, and possibly enriched, data sets.

Another operation 303 may comprise generating, using the one or more local learned models 115, a combined data set which represents, for example, the household data and which may be anonymised so that individual user devices 34, 36, 37, 38, 40 or the first and second users 30, 32 cannot be identified within this data. For example, only the identifier of the first hub 10 may be associated with the combined data set in operation 303.

This operation 303 may be performed before, in parallel with, or subsequent to, operation 302 as shown.

Another operation 304 may comprise determining, using the one or more local learned models 115, global parameters based on the combined data set derived in operation 303.

Another operation 305 may comprise transmitting, to the server 16, the global parameters derived in operation 303 for determining updated global parameters using one or more global learned models stored at the server, based at least partially on the global parameters.

At the server 16, in an operation 306, the global parameters derived in operation 305 are received.

In an operation 307 an updated set of global parameters, based at least partially on the global parameters from the first hub 10, and those from other hubs, are generated and transmitted back to the first hub and possibly other hubs.

Returning to the local hub 10, another operation 308 comprises receiving, from the server 16, the updated global parameters.

Another operation 309 comprises updating and transmitting (although the two can be separate operations) the one or more local learned models 115 using both the local parameters derived in operation 302 and the updated global parameters received in operation 308.

Another operation 310 performed at the user device 24 may comprise receiving a copy of the updated models 115 for performing personalised analytics thereat.

Figure 4:
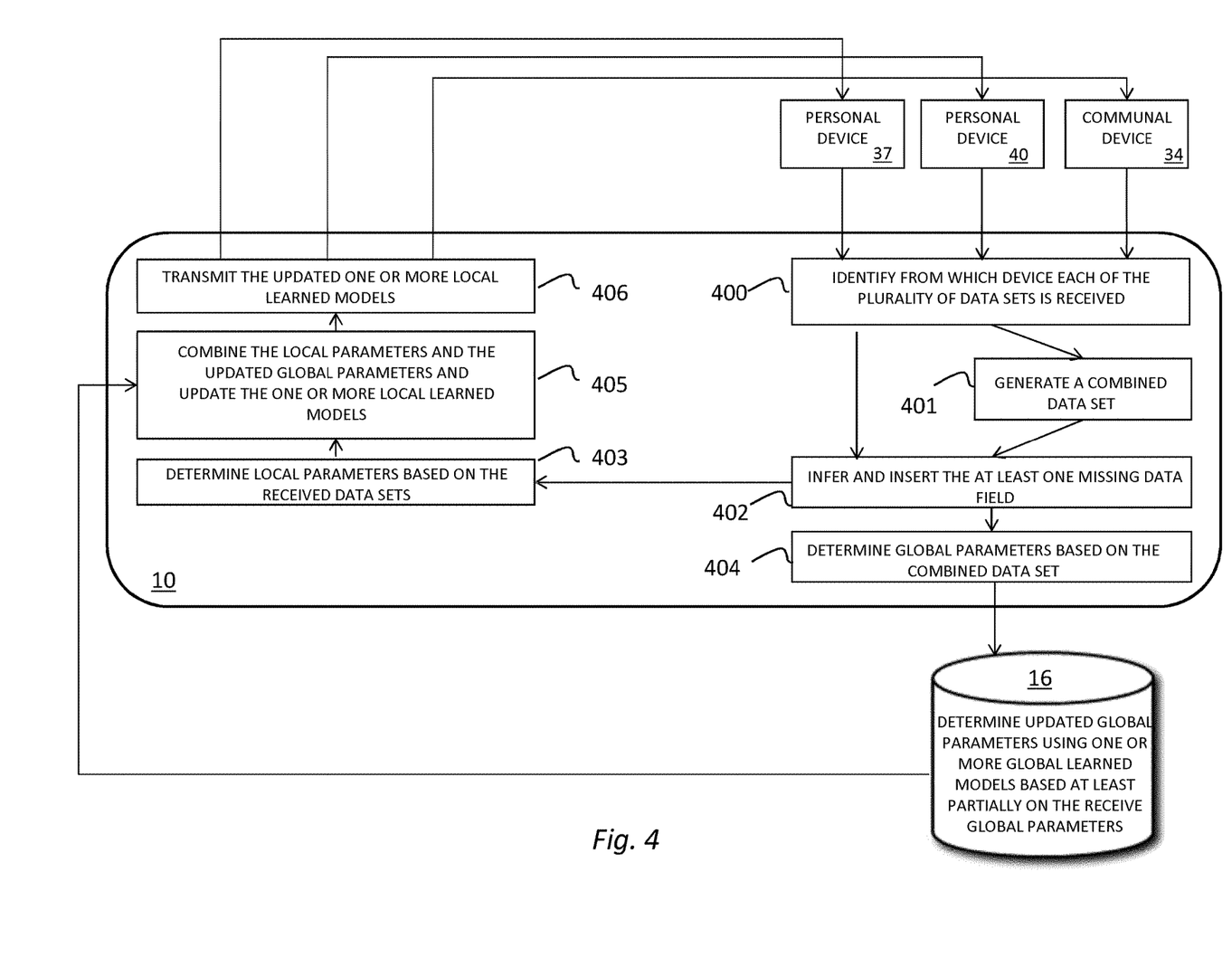
FIG. 4 is a schematic diagram of operations performed at the hub of FIGS. 1 and 2, according to example embodiments.

Referring now to FIG. 4, another embodiment is shown which is useful for understanding operations performed at the first hub 10.

The first hub 10 is shown in relation to a communal device 34 and two personal user devices 37, 40, for example those shown in FIG. 1. The first hub 10 is also shown in relation to the server 16.

A first operation 400 may comprise, after receiving raw data sets from any of the user devices 34, 37, 40, identifying from which device each of the plurality of data sets is derived. This may be by means of identifying an identifier in each data set which is particular to the user device 34, 47, 40 and/or the first or second user 30, 32.

Another operation 401 may comprise generating a combined data set, in which the one or more data sets are combined so as to anonymise the individual first and second users 30, 32 but from which may be identified the individual user devices 34, 37, 40 or their relevant parameters such as heart rate, blood pressure etc.

Another operation 402 may involve converting the sparse combined data set into a combined rich data set using the one or more local learned models 115 and/or standardised data sets given the possibly heterogeneous nature of the data sets from the different user devices 34, 47, 40.

Another operation 403 may comprise using the one or more local learned models 115 to determine local parameters based on the combined rich data set.

Another operation 404, which may be performed before, simultaneously with, or subsequent to, the operation 403, may comprise determining a set of global parameters from the combined rich data set.

The set of global parameters may then be transmitted to the server 16 for generating the updated global parameters as indicated previously.

Another operation 405 may comprise receiving and combining the local parameters and the updated global parameters, received from the server 16, and updating the local learned models 115 based on said combination of parameters.

Another operation 406 may comprise transmitting the updated one or more local learned models to the user devices 34, 37, 40 in order that they may provide personalised analytics to the first and second users 30, 32.

Figure 5:
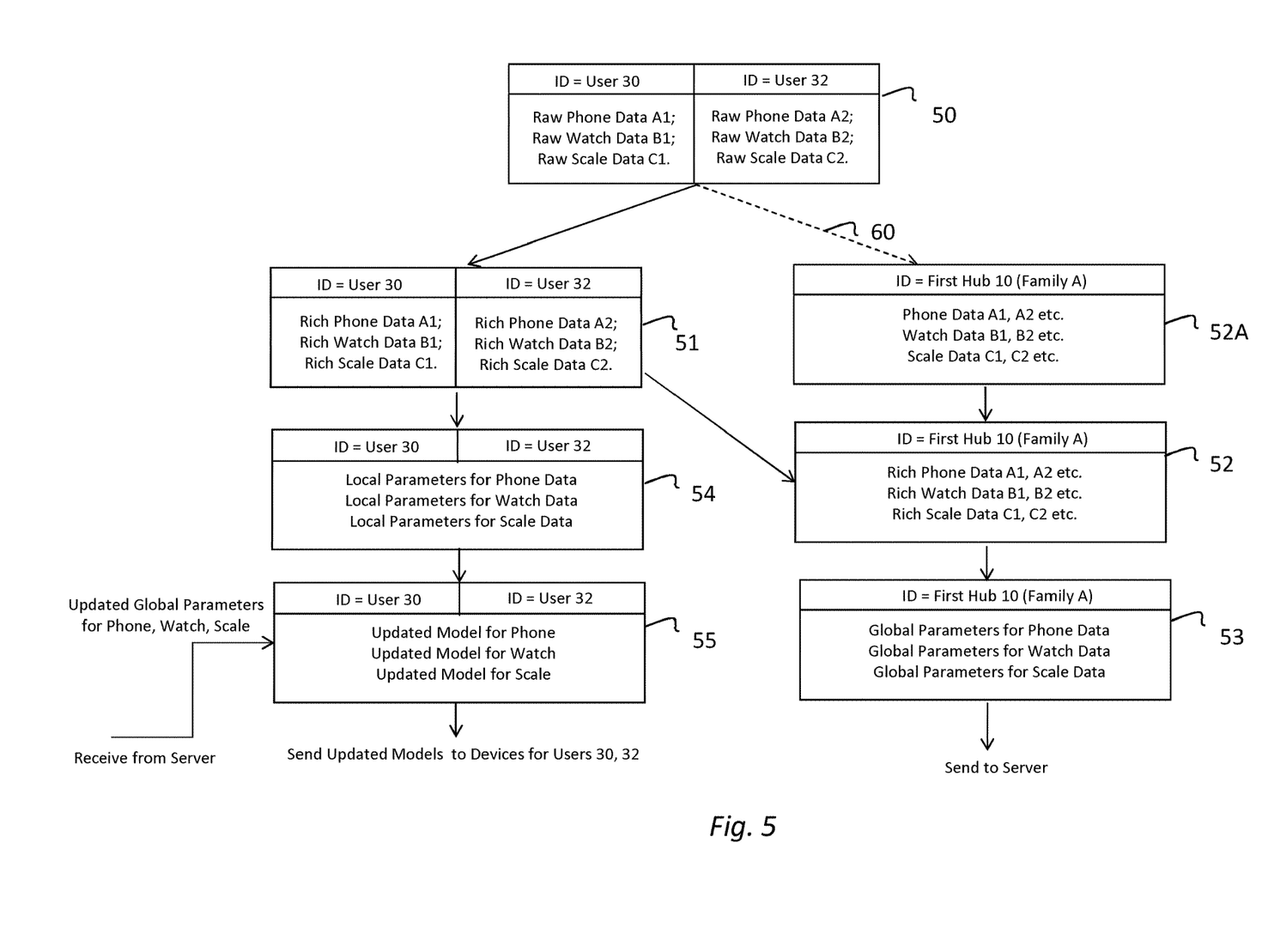
FIG. 5 is a representational view of various data sets received and determined at the hub of FIGS. 1 and 2 in example embodiments.

FIG. 5 is a schematic view of data sets at different stages of embodiments mentioned herein.

A first data set 50 comprises, for the first and second users 30, 32, raw smart phone data A1, A2, raw smart watch data B1, B2 and raw scale data C1, C2. It will be appreciated that other data may be stored on the first hub 10, whether from one or more other user devices and/or from a previous time frame.

A further data set 51 comprises, for the first and second users 30, 32, modified versions of the data A1, A2, B1, B2, C1, C2 which may be enriched data in which missing data is predicted and/or in which data from heterogeneous devices has been standardised.

A further data set 52 is a combined data set comprising, for example, the aggregated or otherwise combined data A1, A2, B1, B2, C1, C2 for each user device, which data set is anonymised without referring to the first and second users 30, 32.

A further data set 52A and arrow 60 is shown to illustrate that the combining operation may be performed on the sparse, raw data A1, A2, B1, B2, C1, C2, prior to enrichment.

A further data set 53 is a set of global parameters for each user device based on the combined data set 52. Hence, the global parameters are anonymised. The global parameters are based on the one or more local models for each of the user devices.

The global parameters 53 are sent to the server 16, not exposing raw data nor the individual users 30, 32.

A further data set 54 is a set of local parameters for each user device based on the non-combined data set 51. Hence, the local parameters are not anonymised. The local parameters are based on the one or more local models for each of the user devices.

A further data set 55 is a set of updated learned models for each user device based on the received local parameters from data set 54, and updated global parameters generated at, and received from, the server 16. The updated global parameters are determined partially based on the global parameters in data set 53 and global parameters similarly determined by other hubs connected to the server 16.

The updated learned models 55 are subsequently provided to the user devices associated with the first and second users 30, 32, which thereby take into account both the localised updates for, for example, the household, and those of a potentially much larger pool of users.

In summary, there are described methods and system for updating learned models, for example for user devices that sense health or activity related data.

Using the system described herein, because raw user data is not sent to any external servers this enables raw user data to be secured easily. A user may therefore opt to use this system because their raw data, which may be personal or sensitive, is less likely to be exposed compared to a centralized training model. Additionally, the system can accommodate the rapid and steady increase of smart devices because only parameters are sent to external servers, and not the raw user data, which may be large data file.

The quantity of raw data on the localised devices enables parameter updates of high quality compared to a decentralized training model. Additionally, because raw user data is used to generate local parameters, personalized analytics can be provided to individual users, this increases the practical effectiveness of the current system compared to a decentralized training model.

In some embodiments, the methods and systems described herein may be applicable to applications other than health or activity monitoring. For example, the so-called Internet of Things (IoT) provides a plurality of networked devices, such as home appliances equipped with sensors, for measuring data associated with a defined property or group, such as thermostatic temperature, energy usage and so on within a home, floor, building or office. It follows that users may wish to understand patterns, trends and/or predictions in such statistical data, for example to understand or predict their next energy bill. The use of a localised hub to collect and aggregate data, and generate updated models based on localised parameters, and updated global parameters received from an external source which takes parameters from many other sources, may therefore use similar principles to those outlined above.

In some embodiments, the functionality performed by the first hub 10 described above may instead be performed on one or more of the user devices 34, 36, 37, 38, 40, most likely the one having the most processing power and/or storage. In some embodiments, the first hub 10 may be used for some of the functionality and one or more of the user devices 34, 36, 37, 38, 40 used for the remaining functionality. In some embodiments, the functionality may be shared across two or more of the user devices 34, 36, 37, 38, 40 in a distributed manner.

It will be appreciated that the above described embodiments are purely illustrative and are not limiting on the scope of the invention. Other variations and modifications will be apparent to persons skilled in the art upon reading the present application.

Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. An apparatus comprising:
at least one processor; and
at least one memory including computer code,
the at least one memory and the computer program code configured to, with the at least one processor, cause the apparatus at least to perform:
receiving, via a local network, a plurality of data sets representing sensed data from one or more devices;
determining, using one or more local learned models, local parameters based on the received data sets;
generating a combined data set by combining the plurality of data sets;
determining, using the one or more local learned models, global parameters based on the combined data set;
causing transmittal of, to a remote system, remote from the apparatus, and via a different network than the local network via which the plurality of the data sets are received, the global parameters for determining updated global parameters using one or more global learned models based at least partially on the global parameters;
receiving, from the remote system, the updated global parameters; and
updating the one or more local learned models using both the local parameters and updated global parameters.

2. The apparatus as claimed in claim 1, wherein the at least one memory and the computer program code are further configured to, with the at least one processor, cause the apparatus at least to perform to:
transmitting, to the one or more devices, the updated one or more local learned models.

3. The apparatus as claimed in claim 1, wherein the one or more devices are members of a predetermined group of devices.

4. The apparatus as claimed in claim 1, wherein the at least one memory and the computer program code and further configured to, with the at least one processor, cause the apparatus at least to perform:
identifying from which device each of the plurality of data sets is received from such that the generated local parameters are particular to each of the identified devices.

5. The apparatus as claimed claim 1, wherein at least one of the received data sets comprises at least one missing data field, and wherein the at least one memory and the computer program code are further configured to, with the at least one processor, cause the apparatus at least to perform:
inferring and inserting the at least one missing data field using the one or more local learned models.

6. The apparatus a claimed in claim 1, wherein the at least one memory and the computer program code and further configured to, with the at least one processor, cause the apparatus at least to perform:
normalizing the plurality of data sets; and/or
using the plurality of data sets to capture high-order correlations.

7. The apparatus as claimed in claim 1, wherein the at least one memory and the computer program code are further configured to, with the at least one processor, cause the apparatus at least to perform:
combining the local parameters and the updated global parameters; and
updating the one or more local learned models using the combined parameters.

8. The apparatus as claimed in claim 1, wherein the at least one memory and the computer program code are further configured to, with the at least one processor, cause the apparatus at least to perform:
combining the plurality of data sets with one or more historical data sets.

9. The apparatus as claimed in claim 1, wherein the plurality of data sets corresponds to different users of a single device.

10. The apparatus as claimed in claim 1, wherein the plurality of data sets correspond to a single user of different respective devices.

11. The apparatus as claimed in claim 1, wherein the data sets represent sensed health or activity data.

12. The apparatus as claimed in claim 11, wherein the one or more devices are portable health monitoring devices and wherein the data sets are received wirelessly from one or more health monitoring devices.

13. The apparatus as claimed in claim 1, wherein the apparatus is a hub device.

14. A method comprising:
receiving, via a local network, a plurality of data sets representing sensed data from one or more devices;
determining, using one or more local learned models, local parameters based on the received data sets;
generating a combined data set by combining the plurality of data sets;
determining, using one or more local learned models, global parameters based on the combined data set;
causing transmittal of, to a remote system, via a different network than the local network via which the plurality of the data sets are received, the global parameters for determining updated global parameters using one or more global learned models based at least partially on the global parameters;
receiving, from the remote system, the updated global parameters; and
updating the one or more local learned models using both the local parameters and updated global parameters.

15. A non-transitory computer readable medium comprising program instructions stored thereon for performing at least the following:
receiving, via a local network, a plurality of data sets representing sensed data from one or more devices;
determining, using one or more local learned models, local parameters based on the received data sets;
generating a combined data set by combining the plurality of data sets;
determining, using one or more local learned models, global parameters based on the combined data set;

transmitting, to a remote system, and via a different network than the local network via which the plurality of the data sets are received, the global parameters for determining updated global parameters using one or more global learned models based at least partially on the global parameters;

receiving, from the remote system, the updated global parameters; and updating the one or more local learned models using both the local parameters and updated global parameters.

16. The apparatus according to claim 1, wherein the data sets and the sensed data are not transmitted to the remote system.

17. The method according to claim 14, wherein the data sets and the sensed data are not transmitted to the remote system.

18. The non-transitory computer readable medium according to claim 15, wherein the data sets and the sensed data are not transmitted to the remote system.

* * * * *

UNITED STATES PATENT AND TRADEMARK OFFICE
CERTIFICATE OF CORRECTION

PATENT NO. : 11,869,662 B2
APPLICATION NO. : 16/954921
DATED : January 9, 2024
INVENTOR(S) : Alberto Gil Ramos et al.

It is certified that error appears in the above-identified patent and that said Letters Patent is hereby corrected as shown below:

In the Claims

In Column 11, Line 63, Claim 5, delete "claimed claim" and insert -- claimed in claim --, therefor.

In Column 12, Line 3, Claim 6, delete "apparatus a" and insert -- apparatus as --, therefor.

Signed and Sealed this
Fifth Day of March, 2024

Katherine Kelly Vidal
*Director of the United States Patent and Trademark Office*